United States Patent
Hellmers et al.

(10) Patent No.: US 11,560,580 B2
(45) Date of Patent: Jan. 24, 2023

(54) PROCESS FOR PRODUCTION OF A SOLID MATERIAL CONTAINING ISOMALTULOSE CRYSTALS AND TREHALULOSE

(71) Applicant: Evonik Operations GmbH, Essen (DE)

(72) Inventors: Frank Hellmers, Grossefehn (DE); Sibylle Schlegel-Kachel, Hanau (DE); Johannes Oehrlein, Duesseldorf (DE); Jan Wolter, Duesseldorf (DE)

(73) Assignee: Evonik Operations GmbH, Essen (DE)

( * ) Notice: Subject to any disclaimer, the term of this patent is extended or adjusted under 35 U.S.C. 154(b) by 569 days.

(21) Appl. No.: 16/485,554

(22) PCT Filed: Feb. 7, 2018

(86) PCT No.: PCT/EP2018/053023
§ 371 (c)(1),
(2) Date: Aug. 13, 2019

(87) PCT Pub. No.: WO2018/149707
PCT Pub. Date: Aug. 23, 2018

(65) Prior Publication Data
US 2020/0048672 A1   Feb. 13, 2020

(30) Foreign Application Priority Data
Feb. 15, 2017 (EP) .................. 17156215

(51) Int. Cl.
*C12P 19/24* (2006.01)
*C12P 19/12* (2006.01)
*C12P 19/44* (2006.01)

(52) U.S. Cl.
CPC ............ *C12P 19/24* (2013.01); *C12P 19/12* (2013.01); *C12P 19/44* (2013.01); *C12Y 504/99011* (2013.01)

(58) Field of Classification Search
CPC .......... C12P 19/24; C12P 19/12; C12P 19/44; C12Y 504/99011
See application file for complete search history.

(56) References Cited

U.S. PATENT DOCUMENTS

2016/0369358 A1* 12/2016 Okuno .................. C13K 13/00
2017/0166939 A1*  6/2017 Harris ............ C12Y 302/01091

FOREIGN PATENT DOCUMENTS

DE     10 2012 216 955 A1    3/2014
EP         2 674 500 A1     12/2013
EP         2 716 771 A1      2/2014

OTHER PUBLICATIONS

Yoshikazu Nakajima, Abstract, Journal of Japanese Socienty of Starch Science, 1988, vol. 35, No. 2, pp. 131-139. (Year: 1988).*
International Search Report and Written Opinion dated May 7, 2018 in PCT/EP2018/053023 filed Feb. 7, 2018.
Kawaguti, H. Y. et al., "Production of isomaltulose obtained by *Erwinia* sp. Cells submitted to different treatments and immobilized in calcium alginate," Ciencia e Tecnologia de Alimentos, vol. 31, No. 1, Jan.-Mar. 2011, pp. 257-263, XP002768649.
Kawaguti, H. Y. et al., "Isomaltulose production by free cells of *Serratia plymuthica* in a batch process," Food Chemistry, vol. 120, 2010, pp. 789-793, XP026858486.
Tang, W-Z., et al., "Advances in isomaltulose production catalyzed by sucrose isomerase," Institute of Microbiology, CAS, vol. 39, No. 9, Sep. 20, 2012, pp. 1314-1322, XP 002768593.
N.N.: "Crystallization of Isomaltulose," GEA Messo PT, https://www.gea.com/de/binaries/TSS01.092013-D.isomaltulose_tom24-21938.pdf, 2017, 2 pages.
Mu, W. et al., "Current studies on sucrose isomerase and biological isomaltulose production using sucrose isomerase," Applied Microbiology and Biotechnology, vol. 98, 2014, pp. 6569-6582, XP002780224.
Hellmers, F. et al., "Robust enzyme immobilizates for industrial isomalt production," Molecular Catalysis, vol. 445, 2017, pp. 293-298, XP002780225.

* cited by examiner

*Primary Examiner* — Allison M Fox
*Assistant Examiner* — Qing Xu
(74) *Attorney, Agent, or Firm* — Oblon, McClelland, Maier & Neustadt, L.L.P.

(57) ABSTRACT

A process for producing a solid material comprising isomaltulose crystals and trehalulose, including: A) contacting an enzyme complex with a sucrose-containing solution; B) isomerizing at least a part of the sucrose to isomaltulose and trehalulose; C) separating off the enzyme complex to obatin a solution including isomaltulose, trehalulose and water; D) partially removing the water by evaporation to obtain a concentrated solution; E) bringing the concentrated solution to a temperature range of 30° C. to 63° C. and subsequently inducing isomaltulose crystallization in this temperature range followed by cooling, thereby obtaining a solid material including isomaltulose crystals and trehalulose.

11 Claims, No Drawings

PROCESS FOR PRODUCTION OF A SOLID MATERIAL CONTAINING ISOMALTULOSE CRYSTALS AND TREHALULOSE

TECHNICAL FIELD

The present invention provides a process for production of a solid material containing isomaltulose crystals and trehalulose comprising the process steps A) bringing an enzyme complex which is able to catalyse the reaction of sucrose to isomaltulose and trehalulose into contact with a sucrose-containing solution;

B) isomerizing at least some of the sucrose to isomaltulose and trehalulose;

C) separating off the enzyme complex to give a solution containing isomaltulose, trehalulose and water;

D) partial removal of the water by evaporation, while obtaining a concentrated solution with, based on the total solution, a solid content of 75 wt % to 95 wt %, preferably 80 wt % to 93 wt %, particularly preferably 86 wt % to 92 wt %;

E) bringing the concentrated solution to a temperature of 30° C. to 63° C., preferably 45° C. to 62° C., even more preferably 55° C. to 60° C., and subsequent induction of isomaltulose crystallisation in this temperature range followed by cooling while obtaining a solid material containing isomaltulose crystals and trehalulose.

PRIOR ART

Isomaltulose ($\alpha$-D-glucopyranosyl-1,6-fructose, also Palatinose®) is a sugar replacer which is obtained from sucrose. Production thereof proceeds via isomerization of sucrose which is generally carried out enzymatically using isomaltulose synthases (sucrose glucosylmutases, EC 5.4.99.11). DE1049800, DE2217628, EP 28900 and EP 91063 describe methods using immobilized bacterial cells for the enzymatic conversion of sucrose to isomaltulose. EP 0625578, for this purpose, uses bacterial strains from the group Protaminobacter *rubrum* (CBS 574.77), *Serratia plymuthica* (ATCC 15928), *Serratia marcescens* (NCIB 8285), *Leuconostoc mesenteroides* (NRRL-B 512 F (ATCC 1083 a)) and *Erwinia rhapontici* (NCPPB 1578). EP 0392556 and EP1257638 describe the use of bacterial strains from the group *Klebsiella terrigena* JCM 1687, *Klebsiella* sp. No. 88 (FERM BP-2838) and *Klebsiella singaporiensis* LX3 and LX21.

These isomerisation methods are carried out using either live or dead cells, with immobilized or free cells: for instance, DE3133123 and EP0915986, for example, describe immobilization methods of enzyme catalysts using calcium alginate or ion exchangers, just as in EP0001099, a method using free, live cells, which can produce isomaltulose in the context of a fermentation.

In the enzymatic reaction of sucrose, as byproducts, trehalulose ($\alpha$-D-glucopyranosyl-1,1-fructose) and also fructose and glucose, are frequently formed.

EP483755 therefore also describes a method for producing trehalulose, in which, substantially the above described method was optimized with respect to the product yield of trehalulose, by using sucrose glucosylmutases of certain *Pseudomonas* or *Agrobacterium* strains.

DE102012216955 discloses a process for the continuous crystallisation of isomaltulose comprising the steps of A) providing a feed solution containing isomaltulose and water, b) partially removing the water by evaporation to obtain a suspension of isomaltulose crystals, C) separating the suspension into an isomaltulose-containing solid and a mother liquor and optionally D) washing the isomaltulose-solid.

EP2674500 discloses a method for producing a solid material from a saccharide liquid comprising isomaltulose, wherein said saccharide liquid is obtained by allowing an enzyme which produces isomaltulose from sucrose to act on a sucrose liquid, wherein said method comprises steps: heating said saccharide liquid to adjust a solid content of said saccharide liquid to 77 to 96 mass %, subjecting a mixture resulting from the aforesaid step to a shearing force to generate crystal nuclei, while keeping a temperature of the product at 65 to 120 degrees Celsius, and cooling the mixture to obtain the solid material.

The disadvantages of the prior art are that either rather pure isomaltulose crystals are obtainable, thereby wasting the included trehalulose, that no crystalline solids are obtained but amorphous solids and that high temperature ranges are worked at, which require large amount of energy.

It was therefore an object of the present invention to provide a process which overcomes at least one disadvantage of the prior art processes.

DESCRIPTION OF THE INVENTION

Surprisingly, it has now been found that the process according to claim 1 is able to achieve this object.

The present invention therefore provides a process for production of a solid material containing isomaltulose crystals and trehalulose comprising the process steps A) bringing an enzyme complex which is able to catalyse the reaction of sucrose to isomaltulose and trehalulose into contact with a sucrose-containing solution;

B) isomerizing at least some of the sucrose to isomaltulose and trehalulose;

C) separating off the enzyme complex to give a solution containing isomaltulose, trehalulose and water;

D) partial removal of the water by evaporation, while obtaining a concentrated solution with, based on the total solution, a solid content of 75 wt % to 95 wt %, preferably 80 wt % to 93 wt %, particularly preferably 86 wt % to 92 wt %;

E) bringing the concentrated solution to a temperature of 30° C. to 63° C., preferably 45° C. to 62° C., even more preferably 55° C. to 60° C., and subsequent induction of isomaltulose crystallisation in this temperature range followed by cooling while obtaining a solid material containing isomaltulose crystals and trehalulose.

One advantage of the process according to the invention is the constant product quality.

Yet a further advantage of the process according to the invention is that an increased apparatus-specific space-time yield is achieved.

Yet a further advantage of the process according to the invention is that seed crystals and their complex growth are not needed.

A further advantage of the process according to the invention is the possible saving in energy, as the process can be run at low temperatures.

Yet a further advantage of the process according to the invention is that the yields are higher, as more product is solidified compared to mere crystallization processes that focus on pure isomaltulose.

Another advantage of the instant invention is the fact, that the obtained product is ready to use and does not need extended time periods for crystal formation to complete.

The term "isomaltulose" is to be understood as meaning 6-O-$\alpha$-D-glucopyranosido-D-fructose.

The term "trehalulose" is to be understood as meaning 1-O-α-D-glucopyranosido-D-fructose.

The term "enzyme complex" is to be understood as meaning a composition or mixture composition having at least one active enzyme, which may also be complex in nature, such as, for example, a living cell. Further examples of an enzyme complex are fusion proteins in which the at least one active enzyme is linked to at least one further polypeptide, but also a purified enzyme itself can be an enzyme complex for the purposes of the present invention.

In connection with the present invention, the term "immobilized enzyme complex" is to be understood as meaning an enzyme complex which is bonded to a matrix or is enclosed by a matrix such that the enzyme complex is restricted, for example slowed, in its free diffusion or in its free movement in an aqueous solution.

In connection with the present invention, the term "solid material containing isomaltulose crystals and trehalulose" is to be understood as meaning solid material which contains at least 50 wt %, preferably at least 70 wt %, even more preferred at least 90 wt %, crystalline matter, based on the total solid material. The method suited for determining the crystal content is X-ray diffraction.

Given weight values of substances refer to anhydrous substances.

Unless stated otherwise, all percentages (%) given are percentages by mass.

In the process according to the invention, a sucrose concentration of 20-80% by weight, in particular of 30-50% by weight, is present in the sucrose-containing solution of process step A), based on the total sucrose-containing solution.

A preferred process according to the invention is especially suited for the production of a solid material containing isomaltulose crystals and trehalulose which comprises isomaltulose in an amount of 70 to 90 wt %, especially 72 to 89 wt %, more especially 74 to 88 wt %, more especially 75 to 85 wt %, relative to the total wt of the dry solid material. The solid material containing isomaltulose crystals and trehalulose comprises trehalulose in an amount of 5 to 25 wt %, especially 6 to 20 wt %, relative to the total wt of the dry solid material.

The solid material containing isomaltulose crystals and trehalulose may comprise glucose in an amount of 0.1 to 5 wt %, especially 0.2 to 4 wt %, relative to the total wt of the dry solid material.

The solid material containing isomaltulose crystals and trehalulose may comprise fructose in an amount of 0.1 to 5 wt %, especially 0.2 to 4 wt %, relative to the total wt of the dry solid material.

The solid material containing isomaltulose crystals and trehalulose may comprise sucrose in an amount of 0.05 to 4 wt %, especially 0.1 to 3 wt %, relative to the total wt of the dry solid material.

Preferably the solid material containing isomaltulose crystals and trehalulose contains all three of the aforementioned sugars.

The enzyme present in the enzyme complex is preferably at least one sucrose glucosylmutase of the enzyme class EC 5.4.99.11. Particular preference is given to using sucrose glucosylmutases from Protaminobacter *rubrum*, in particular the strain Protaminobacter *rubrum* CBS 574.77; Protaminobacter *ruber* Z12; Serratia *plymuthica*, in particular the strain Serratia *plymuthica* ATCC 15928; Serratia *odorifera*, in particular the strain Serratia *odorifera* 4Rx13; Serratia *marcescens*, in particular the strain Serratia *marcescens* NCIB 8285; Leuconostoc *mesenteroides*, in particular the strain Leuconostoc *mesenteroides* ATCC 1083 a; Erwinia *rhapontici*, in particular the strains Erwinia *rhapontici* ATCC29283, NCPPB 1578, DSM 4484, NX-5 and WAC2928, Erwinia sp., in particular the strain Erwinia sp. D12; Agrobacterium *radiobacter*, in particular the strain Agrobacterium *radiobacter* MX-232; Klebsiella *terrigena*, in particular the strain Klebsiella *terrigena* JCM 1687; Klebsiella sp., in particular the strains Klebsiella sp. FERM BP-2838, LX3 and NK33-98-8; Klebsiella *pneumoniae*, in particular the strain Klebsiella *pneumoniae* 342; Klebsiella *singaporensis*, in particular the strain Klebsiella *singaporensis* LX21; Pseudomonas *mesoacidophila*, in particular the strain Pseudomonas *mesoacidophila* MX-45; Pantoea *dispersa*, in particular the strain Pantoea *dispersa* UQ68J; Klebsiella *planticola*, in particular the strains Klebsiella *planticola* CCRC 19112, MX10 and UQ14S; Enterobacter sp., in particular the strain Enterobacter sp. FMB-1 (Seq ID No. 16), SZ62 and Ejp617; Azotobacter *vinelandii* DJ in the process according to the invention, with Protaminobacter *rubrum* CBS 574.77 and Protaminobacter *ruber* Z12 being particularly preferred.

The enzymes can be used in purified form as polypeptides. For ease of purification, these can be in the form of fusion proteins, where, for example, a tag permitting ease of purification, such as for example a His tag, a Strep tag, a GST tag or an MBP tag, is fused to the enzyme.

In the process according to the invention, it is preferred that the enzyme complex is whole cells which are preferably selected from the group Protaminobacter *rubrum*, in particular the strain Protaminobacter *rubrum* CBS 574.77; Protaminobacter *ruber* Z12; Serratia *plymuthica*, in particular the strain Serratia *plymuthica* ATCC 15928; Serratia *odorifera*, in particular the strain Serratia *odorifera* 4Rx13; Serratia *marcescens*, in particular the strain Serratia *marcescens* NCIB 8285; Leuconostoc *mesenteroides*, in particular the strain Leuconostoc *mesenteroides* ATCC 1083 a; Erwinia *rhapontici*, in particular the strains Erwinia *rhapontici* ATCC29283, NCPPB 1578, DSM 4484, NX-5 and WAC2928; Erwinia sp., in particular the strain Erwinia sp. D12; Agrobacterium *radiobacter*, in particular the strain Agrobacterium *radiobacter* MX-232; Klebsiella *terrigena*, in particular the strain Klebsiella *terrigena* JCM 1687; Klebsiella sp., in particular the strains Klebsiella sp. FERM BP-2838, LX3 and NK33-98-8; Klebsiella *pneumoniae*, in particular the strain Klebsiella *pneumoniae* 342; Klebsiella *singaporensis*, in particular the strain Klebsiella *singaporensis* LX21; Pseudomonas *mesoacidophila*, in particular the strain Pseudomonas *mesoacidophila* MX-45; Pantoea *dispersa*, in particular the strain Pantoea *dispersa* UQ68J; Klebsiella *planticola*, in particular the strains Klebsiella *planticola* CCRC 19112, MX10 and UQ14S; Enterobacter sp., in particular the strain Enterobacter sp. FMB-1, SZ62 and Ejp617; Azotobacter *vinelandii* DJ, with Protaminobacter *rubrum* CBS 574.77 and Protaminobacter *ruber* Z12 being particularly preferred. The whole cell preferably included in the preferred process according to the invention can be in any state, like growing, resting, alive or dead, wherein resting cells are particularly preferred.

The immobilization of the enzyme complexes can take place for example in the form of CLEAs (insoluble cross-linked enzyme aggregates) (Cao, L. et al., 2000, *Cross-linked enzyme aggregates: a simple and effective method for the immobilization of penicillin acylase*, Org. Lett., 2: 1361-1264) or on solid support materials of natural or synthetic origin. Natural materials are e.g. polysaccharides such as alginate, agarose, sepharose, cellulose and derivatives thereof (e.g. DEAE- or CM-cellulose). It is also possible to use modified sepharoses, such as e.g. epoxy-activated, bromocyanogen-activated, NHS-activated, thiol-activated sepharose. These sepharoses are commercially available for example from the companies GE Healthcare, BioRad, Sigma and Pierce.

Synthetic organic polymers which can be used are polystyrene derivatives, polyacrylates, in particular epoxide-activated acrylic resin beads (Eupergit), polymethacrylates, polyacrylamides, vinyl and allyl polymers, polyesters or polyamides.

Preferred poly(meth)acrylates are selected from C1-C10-alkyl acrylate polymers, C1-C10-alkyl methacrylate polymers and C1-C10-alkyl acrylate-C1-C10-alkyl methacrylate copolymers. A process for encapsulation and further preferably used poly(meth)acrylatepolymers are described in EP3114218.

Possible inorganic carriers are materials based on silicon oxides or aluminium oxides, or mixtures thereof.

The immobilization of the enzyme complexes can also take place by encapsulation in polymeric porous gels e.g. hydrophobic sol-gel materials of $RSi(OCH_3)_3$ or mixtures of $RSi(OCH_3)_3$ and $Si(OCH_3)_4$ (Reetz, M. T.; Zonta, A.; Simpelkamp, J.; Rufinska, A.; Tesche, B. J. Sol-Gel Sci. Technol. 1996, 7, p. 35-43) or of porous polymeric silica gels (Elgren, T. M.; Zadvorny, O. A.; Brecht, E.; Douglas, T.; Zorin, N. A.; Maroney, M. J. & Peters, J. W.).

Moreover, besides an immobilization, a multiuse of the enzyme in enzyme membrane reactors is conceivable.

The enzyme complexes used in the process according to the invention, in particular cells, are preferably immobilized in polysaccharides such as alginate, pectin, carrageenan, chitosan or polyvinyl alcohols, such as, for example, lentikats, or mixtures thereof, in particular in alginate; cf. in this regard for example Shimizu, H., et al. (1997) *Screening of novel microbial enzymes for the production of biologically and chemically useful compounds, in: Advances in biochemical engineering biotechnology*, Vol 58: *New Enzymes for Organic Synthesis* (Scheper, T., ed.) pp. 45-88, Springer, New York.

A particularly preferred immobilization to be used for any form of the enzyme complexes used in the process according to the invention is the process described in EP2011865, in which the enzyme complexes immobilized on an inert support are provided with a silicone coating obtained by hydrosilylation.

It is preferred according to the invention that in process step B), a pH of from 4 to 9.5 is present. This pH is advantageously established with the help of an acid, in particular an inorganic acid, preferably from the group sulphuric acid, hydrochloric acid or acetic acid.

It is also preferred according to the invention that in process step B), a temperature of from 20 to 40° C., preferably from 25 to 35° C., measured in the sucrose-containing solution, is present.

In process step C), the enzyme complex and eventually included solid impurities are separated off from the isomaltulose; this takes place for example by filtration, sedimentation, ion exchange chromatography or centrifugation. On account of the immobilizate character of the enzyme complex, this separation is facilitated compared with nonimmobilized enzyme.

For reasons of process economy, it is preferred according to the invention if the immobilized enzyme complex is used in the form of a solid bed through which the sucrose-containing solution flows (H. Schiweck, Zuckerind. (1990), 115 (7), 555-565). Corresponding solid-bed processes are described in A. Liese, et. al. Processes in A. Liese, K. Seelbach, C. Wandrey (Eds.), *Industrial Biotransformations 2nd Edition* (2006), Wiley-VCH, Weinheim.

It might be advantageous if eventually included solid impurities are separated off from the isomaltulose by sedimentation. This preferably is achieved by storage over a period of time from 2 days to 60 days, preferably 10 days to 50 days, more preferably from 20 days to 40 days, preferably in a temperature range from 2° C. to 30° C., preferably from 3° C. to 25° C., particularly preferably from 4° C. to 12° C., whilst eventually included solid impurities sink to the bottom of the solution containing isomaltulose, trehalulose and water.

This has the surprising technical effect, that induction of isomaltulose crystallization can be induced at temperatures as low as 30° C. Therefore; an alternatively preferred process according to the invention is characterized in that in process step C) the enzyme complex and eventually included solid impurities are separated off from the isomaltulose by storage over a period of time from 2 days to 60 days, preferably together with the features that in step D) the water is removed by evaporation, while obtaining a concentrated solution with, based on the total solution, a solid content of 86 wt % to 92 wt % and that in step E) the concentrated solution is brought to a temperature of 30° C. to 50° C., By varying the degree of evaporation, different solid contents can be achieved; this can be controlled via the residence time in process step D), for example.

A process preferred according to the invention is characterized in that process step D) is carried out in a temperature range from 50° C. to 80° C., preferably from 60° C. to 75° C., particularly preferably from 63° C. to 68° C., and in a pressure range from 70 mbar to 200 mbar, preferably from 100 mbar to 180 mbar, particularly preferably from 130 mbar to 160 mbar. In particular, it is preferred in this context that, in the process according to the invention, process step D) is carried out in a temperature range from 63° C. to 68° C., and in a pressure range from 130 mbar to 160 mbar.

An alternatively preferred process according to the invention is characterized in that process step D) is carried out in a temperature range from 50° C. to 80° C., preferably from 60° C. to 75° C., particularly preferably from 63° C. to 68° C., and in a pressure range from 250 mbar to 500 mbar, preferably from 275 mbar to 450 mbar, particularly preferably from 300 mbar to 400 mbar. In particular, it is preferred in this context that, in the process according to the invention, process step D) is carried out in a temperature range from 63° C. to 68° C., and in a pressure range from 300 mbar to 400 mbar.

A still further alternatively preferred process according to the invention is characterized in that process step D) is carried out in a temperature range from 95° C. to 130° C., preferably from 106° C. to 121° C., particularly preferably from 108° C. to 118° C., and in a pressure range from 250 mbar to 500 mbar, preferably from 275 mbar to 450 mbar, particularly preferably from 300 mbar to 400 mbar. In particular, it is preferred in this context that, in the process according to the invention, process step D) is carried out in a temperature range from 108° C. to 118° C., and in a pressure range from 300 mbar to 400 mbar.

By varying the degree of evaporation, different solids contents and/or yields can be achieved; this can be controlled via the residence time, the pressure and the temperature in process step D), for example. Evaporation can take place in a continuous or a batch evaporator.

It is preferred according to the invention that in process step D), a pH of from 3.5 to 9.5 is present.

In process step E) the concentrated solution is brought to a temperature of 30° C. to 63° C., preferably 45° C. to 62° C., even more preferably 55° C. to 60° C., preferably at ambient pressure. It is especially preferred if according to the invention in process step D) a concentrated solution with, based on the total solution, a solid content of 86 wt % to 92 wt % is obtained and in process step E) the concentrated solution is brought to a temperature of 55° C. to 60° C.

A process preferred according to the invention is characterized in that, in process step E) the concentrated solution is brought to a temperature of 30° C. to 63° C., preferably 45° C. to 62° C., even more preferably 55° C. to 60° C., and subsequently isomaltulose crystallisation is induced by the means selected from at least one of the group consisting of addition of isomaltulose seed crystals, shearing forces, agitation, friction, radiation and ultrasound, with shearing forces particularly preferred. In this context it is extraordinary preferred that isomaltulose crystallisation is induced by the means selected of shearing forces but without the addition of isomaltulose seed crystals.

A process preferred according to the invention is characterized in that, if in process step E) isomaltulose seed crystals are added, these are added in an amount of from 0.01% to 10% by weight and particularly preferably 0.1% to 1% by weight, based on the total amount of isomaltulose contained in the concentrated solution.

A process preferred according to the invention is characterized in that, in process step E) shearing forces induce isomaltulose crystals by a shearing force-applying device, preferably without the addition of isomaltulose seed crystals.

In the present invention, "a shearing force-applying device" is a device which applies a shearing force on a material. This can be for example a device which is capable of kneading a highly viscous material, therefore a device by which forces of shifting a material are applied in one direction and an opposite direction to grind, knead, or mix the material. This can especially be a device having a function as a kneader, more especially a device which can heat and scrape a material so that the processed material is not left, adhered to a vessel of the device. The device may be a kneader, an extruder, a kneader, an agitator, and a universal mixing and agitating machine, wherein an extruder is preferably used.

These shearing force-applying device can be a small laboratory kneader having a double-walled vessel with a volume of 100-300 ml. This device preferably has a rotational speed of 10-40 rpm more preferably of 20-40 rpm. The device may have a horizontal kneading trough with two co-rotating kneading blades and the maximum torque of the device may be 40 Nm or 30 Nm. The temperature of the product may be adjusted via a thermal fluid in a double walled jacket. As example an IKA HKD-T 06 is named. The product n this device is moved in a circular motion and sheared between the kneading blades. IN this device the time period required for complete crystallization and formation of a white solid product (referred to as "processing time" hereinafter) may be 1-40 min, preferably 3-15 min. During the processing time shearing forces are applied continuously to the isomaltulose mixture by kneading and agitation. The kneading device is operated in a batch mode. After completion of the processing time the product is removed from the kneading trough.

As a continuous shearing-force applying device a laboratory extruder, especially a co-rotating twin-screw extruder, for example a Haake PolyLab OS, may be employed. The length to diameter ratio of the screw (LID) may be 25. The screw may be configured to contain transport and kneading elements. The material is transported horizontally from the feeding port to the discharge end of the extruder. The product is sheared in the screw and in particular in between the kneading elements. The maximum torque of the device may be 130 Nm or 100 Nm. The extruder may possess an electrical heating of the extruder barrel. The rotational speed of the extruder may be 5-100 rpm, preferably 10-50 rpm. The processing time in the extruder may be 20 sec to 5 min, preferably 30 sec to 2 min.

As a larger scale shearing-force applying device a kneader-extruder, especially a kneader with a single rotating feed screw may be used. The screw may contain transport and kneading elements. The material is transported horizontally from the feeding port to the discharge end of the extruder. The product is sheared in the screw and in particular in between the kneading elements.

A process preferred according to the invention is characterized in that, in process step E) induction of isomaltulose crystallisation by ultrasound is achieved by sonication with a specific surface power density in a range from 20 W/cm$^2$ to 400 W/cm$^2$, in particular 80 W/cm$^2$-300 W/cm$^2$, in particular 120 W/cm$^2$-180 W/cm$^2$.

It is preferred according to the invention that in process step E), a pH of from 3.5 to 9.5 is present.

The examples listed below describe the present invention by way of example without any intention of limiting the invention, the scope of which arises from the entire description and the claims, to the embodiments specified in the examples.

EXAMPLES

Example 1: Isomerization of Sucrose-Containing Solution

For all experiments isomerization was carried out as follows:

Cells from a subculture of the strain Protaminobacter rubrum (CBS574.77) were elutriated with 1-5 ml of a sterile nutrient medium consisting of 50 g/kg of sucrose, 15 g/kg of corn swell water, 7 g/kg of ammonium sulphate, 0.5 g/kg of yeast extract, 1 g/kg of potassium dihydrogensulphate, 0.41 g/kg of magnesium chloride heptahydrate, 0.004 g/kg of manganese chloride tetrahydrate, 0.047 g/kg of iron citrate monohydrate and 926 g/kg of water, if necessary adjusted to pH 7.2. This suspension served as inoculum for the preculture, which comprises 200 ml of the above nutrient solution in a 1 l shake flask.

After cultivation at 30° C. for 20 hours, a 2 l fermenter, with one litre of sterile production medium consisting of 50 g/kg of sucrose, 15 g/kg of corn swell water, 3 g/kg of ammonium sulphate, 4 g/kg of ammonium hydrogenphosphate, 0.5 g/kg of yeast extract, 1 g/kg of potassium dihydrogensulphate, 0.41 g/kg of magnesium chloride heptahydrate, 0.004 g/kg of manganese chloride tetrahydrate, 0.047 g/kg of iron citrate monohydrate and 926 g/kg of water, adjusted to pH 7.2, was inoculated with the preculture in such a way that the initial optical density (0D600) was 1.

Fermentation was carried out at 30° C., pH 7 (regulated) and a $pO_2$ of 30% (cascade stirrer, Airflow). Sucrose was fed in during the fermentation. After 15-20 h, the fermentation process was complete and the biomass could be harvested for the immobilization.

For this purpose, the resulting suspension was mixed with water and a 4% strength alginate solution in the volume ratio 1:1. This suspension was then immobilized by dropping in a 2% strength $CaCl_2$) solution. The resulting beads were post-cured with polyethyleneimine and glutaraldehyde. The resulting biocatalyst can be stored for several weeks at 4-10° C. The immobilized cells obtained are introduced into a heatable column reactor and heated to 20-35° C., and diluted thick juice from sugar beets with a content of 41% by weight of sucrose, based on the total thick juice, is passed through in a continuous stream.

The composition after isomerization can be found in Table 1.

TABLE 1

Composition of isomerized thick juice

| Fructose | [% by wt.] | 1.4% |
| Glucose | [% by wt.] | 0.5% |
| Sucrose | [% by wt.] | 1.7% |
| Isomaltulose | [% by wt.] | 32.5% |
| Trehalulose | [% by wt.] | 3.8% |
| Isomelezitose | [% by wt.] | 1.1% |
| Water | [% by wt.] | 59.0% |

Example 2: Sedimentation

For some experiments eventually included solid impurities were separated off from the isomaltulose by sedimentation by storage at 20° C. over a period of time of 30 days.

Example 3: Concentration

The solution containing isomaltulose, trehalulose and water was concentrated in a rotary evaporator at 65° C. and 130 mbar to the desired solid content between 85 and 98%. The pressure was lowered to 110 mbar during the evaporation process to compensate for the falling vapor pressure of the concentrated solution. At the end of the evaporation process the temperature was raised to 95° C. at 150 mbar to obtain a pourable syrup.

Given water content values below in percent equal to 100 wt %-wt % solid content.

Example 4: Crystallization

Crystallization was induced in a Thermo Fischer continuous twin screw extruder (Haake PolyLab OS PTW 16/25) with kneading and transport elements. The concentrated syrup was transferred into the heated (~140° C.) feed funnel of the extruder.

Crystallization induction at higher temperatures gives a product which is less easy to handle and needs higher energy amounts (C1 and C2). Too highly concentrated solutions cannot be crystallized properly (C3). The very useful crystalline masses that are formed at the temperatures according to the instant invention can be processed further very easily and deliver a ready to use, very homogenous product of a pleasant appearance.

| Experiment | C1 | C2 | C3 | E1 |
|---|---|---|---|---|
| Water content [—] | 9% | 10% | 2% | 10% |
| Tproduct [° C.] | 76 | 75 | 56.2 | 55 |
| Rotational speed [min−1] | 18 | 10 | 10 | 10 |
| Torque [Nm] | 25 | 7 | 5.5 | 32 |
| Seed crystals | yes | no | no | no |
| Sedimentation | — | 30 d | 30 d | — |
| Result | dry and hard, brittle crystallized product, small mass flow due to blocking of screw | turbid, viscous liquid mass, solidifies and crystallizes upon cooling | Slightly turbid melt that stays rubbery upon cooling | crystalline white solid strands |

| Experiment | E2 | E3 | E4 | E5 |
|---|---|---|---|---|
| Water content [—] | 10% | 14% | 12% | 8% |
| Tproduct [° C.] | 62 | 48.9 | 33.5 | 58.5 |
| Rotational speed [min−1] | 20 | 5 | 5 | 10 |
| Torque [Nm] | 6 | 4.3 | 43.2 | 32.4 |
| Seed crystals | no | no | no | no |
| Sedimentation | — | 30 d | 30 d | 30 d |
| Result | crystalline white solid strands | white, soft, shiny crystalline strands that solidify and become matte upon cooling | white, soft, shiny crystalline strands that solidify and become matte upon cooling | white, soft, matte, crystalline strands that solidify upon cooling |

The invention claimed is:

1. A process for producing a solid material comprising isomaltulose crystals and trehalulose, the process comprising:
    A) contacting an enzyme complex with a sucrose-comprising solution, wherein the enzyme complex is capable of catalyzing a reaction of converting sucrose to isomaltulose and trehalulose;
    B) isomerizing at least a part of the sucrose in the sucrose-comprising solution to isomaltulose and trehalulose;
    C) separating off the enzyme complex, thereby obtaining a solution comprising isomaltulose, trehalulose and water;
    D) partially removing the water from the solution by evaporation at a first temperature, thereby obtaining a concentrated solution with a solid content of 86 wt % to 92 wt %, based on a total weight of the concentrated solution; and
    E) bringing the concentrated solution to a second temperature, which is within a temperature range of 55° C. to 60° C. and is different from the first temperature, and subsequently inducing isomaltulose crystallization in the temperature range of 55° C. to 60° C. followed by cooling, thereby obtaining the solid material comprising isomaltulose crystals and trehalulose.

2. The process of claim 1, wherein the sucrose-comprising solution of A) has a sucrose concentration of 20-80% by weight, based on a total weight of the sucrose-comprising solution.

3. The process of claim 1, wherein the enzyme complex comprises at least one sucrose glucosylmutase of the enzyme class EC 5.4.99.11.

4. The process of claim 1, wherein the isomerizing in B) is conducted at a pH in a range from 3.5 to 9.5.

5. The process of claim 1, wherein in C), the enzyme complex and solid impurities are separated off from the solution comprising isomaltulose, trehalulose and water by filtration, sedimentation or centrifugation.

6. The process of claim 1, wherein in D), the first temperature is within a temperature range of from 63° C. to 68° C., and the partial removing of the water is carried out in a pressure range of from 130 mbar to 160 mbar.

7. The process of claim 1, wherein the isomaltulose crystallization is induced by at least one selected from the group consisting of addition of isomaltulose seed crystals, shearing forces, agitation, friction, radiation and ultrasound.

8. The process of claim 1, wherein the solid material comprising isomaltulose crystals and trehalulose comprises isomaltulose in an amount of 70 to 90 wt %, trehalulose in an amount of 5 to 25 wt %, glucose in an amount of 0.1 to 5 wt %, fructose in an amount of 0.1 to 5 wt %, and sucrose in an amount of 0.05 to 4 wt %, relative to a total dry weight of the solid material.

9. The process of claim 1, wherein the isomaltulose crystallization is induced without addition of isomaltulose seed crystals.

10. The process of claim 1, wherein the isomaltulose crystals are in the form of crystalline strands.

11. The process of claim 1, wherein in C), the enzyme complex and solid impurities are separated off from the isomaltulose by sedimentation by storage over a period from 2 days to 60 days until the enzyme complex and solid impurities sink to a bottom of the solution comprising isomaltulose, trehalulose and water.

* * * * *